United States Patent
Reed et al.

(10) Patent No.: US 7,917,194 B1
(45) Date of Patent: Mar. 29, 2011

(54) METHOD AND APPARATUS FOR DETECTING PULMONARY EDEMA

(75) Inventors: Derrick W. Reed, Santa Monica, CA (US); Yougandh Chitre, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 392 days.

(21) Appl. No.: 11/560,279

(22) Filed: Nov. 15, 2006

(51) Int. Cl.
*A61B 5/04* (2006.01)
(52) U.S. Cl. ....................................................... 600/509
(58) Field of Classification Search .................. 600/509, 600/529, 547, 484
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 5,876,353 A | 3/1999 | Riff | |
| 5,957,861 A | 9/1999 | Combs et al. | |
| 6,697,672 B2 | 2/2004 | Andersson | |
| 6,931,272 B2 * | 8/2005 | Burnes | 600/509 |
| 7,025,729 B2 | 4/2006 | de Chazal et al. | |
| 7,096,061 B2 * | 8/2006 | Arad | 600/547 |
| 7,467,012 B1 * | 12/2008 | Park et al. | 607/20 |
| 2005/0085734 A1 * | 4/2005 | Tehrani | 600/484 |

\* cited by examiner

*Primary Examiner* — Carl H Layno
*Assistant Examiner* — Pamela M Bays

(57) ABSTRACT

Conditions resulting from acute decompensation such as pulmonary edema may be indicated based on analysis of respiration signals. In some embodiments a respiration signal is derived from an intracardiac electrogram ("IEGM") signal. In some embodiments one or more non-rate-based parameters are derived from a detected respiration signal to identify a pulmonary edema condition. In some embodiments a warning may be generated or therapy administered to a patient in response to an indication of pulmonary edema.

11 Claims, 8 Drawing Sheets

METHOD AND APPARATUS FOR DETECTING PULMONARY EDEMA

TECHNICAL FIELD

This application relates generally to medical applications, and to detection of acute decompensation and pulmonary-related conditions.

BACKGROUND

The health of many patients who have had a heart attack may deteriorate over time due to progressive heart failure. For example, a heart attack often results in damage to a portion of the heart tissue. To compensate for the reduction in heart function due to damaged heart tissue, walls of the heart wall may thicken to enable the heart to pump harder. However, the resulting enlargement of the heart tends to reduce the ejection fraction of the heart.

Progressive heart failure also may affect the timing of contractions in the heart. For example, the normally coordinated pumping of the right ventricle and the left ventricle may become unsynchronized. Cardiac resynchronization therapy ("CRT") may be used to treat such a condition in some patients. Here, an implantable cardiac device incorporating appropriate CRT functionality may be implanted in the patient along with associated leads capable of providing stimulation pulses to the heart.

Although CRT may provide some improvement in heart function, the problems caused by progressive heart failure may eventually lead to acute decompensation and associated pulmonary-related conditions. In particular, a condition known as pulmonary edema may develop whereby fluid accumulates in the patient's lungs. In its early stages, a patient may not be aware that he or she has pulmonary edema. If pulmonary edema is not detected and treated in its early stages, however, hospitalization of the patient may be required to treat the condition. Consequently, there is a need for improved techniques for detecting pulmonary edema to reduce the potential impact on the patient's quality of life and to avoid significant hospital expense that may otherwise result from a failure to detect pulmonary edema at an early stage.

SUMMARY

A summary of various aspects and/or embodiments of an apparatus constructed or a method practiced according to the invention follows. For convenience, one or more embodiments of an apparatus constructed or a method practiced according to the invention may be referred to herein simply as an "embodiment."

The invention relates in some aspects to detection of conditions resulting from acute decompensation including pulmonary-related conditions such as pulmonary edema. For convenience, such conditions may be referred to herein simply as "pulmonary edema." One symptom of pulmonary edema is a change in a patient's respiration pattern. For example, the patient's respiration may become relatively rapid and shallow. Accordingly, in some embodiments an apparatus may be adapted to monitor the respiration of a patient to generate an indication of pulmonary edema. To this end, the apparatus may derive one or more parameters from detected respiration signals and monitor these parameters over time to identify any changes in the parameters that indicate a pulmonary edema condition.

In some embodiments a respiration signal is derived from an intracardiac electrogram ("IEGM") signal. Here, an apparatus may be coupled to one or more implanted cardiac leads that are adapted to sense cardiac electrical activity. The apparatus may thereby derive one or more morphological features from a sensed IEGM signal and use these features to filter a respiration-induced modulation signal from the IEGM signal. The apparatus may then extract various parameters from the resulting respiration signal and monitor these parameters over time to detect any changes in the parameters that indicate a pulmonary edema condition.

In some embodiments one or more non-rate-based parameters are derived from a detected respiration signal to identify a pulmonary edema condition. For example, a pulmonary edema indication may be based on changes in amplitude of the respiration signal, a pulse width of the respiration signal or morphology data representative of the respiration signal.

In some embodiments a pulmonary edema indication may be based on a comparison of a parameter or feature derived from a detected respiration signal with a baseline parameter or feature. Here, the parameters or features may be acquired under similar conditions. Such conditions may include, for example, a time of day, a patient activity level, a patient position or other suitable conditions.

In some embodiments an apparatus for detecting pulmonary edema may be incorporated into an implantable medical device. In some applications the device may comprise an implantable cardiac device. Such an implementation may be particularly advantageous in embodiments that utilize the IEGM signal because the device may already detect the IEGM signal for cardiac stimulation operations.

In some embodiments a warning may be generated in response to an indication of pulmonary edema. For example, an apparatus may generate one or more of an audible signal, a vibratory signal, or a tissue tickler signal. In some embodiments an indication may be sent to an external apparatus that then generates a warning signal.

In some embodiments a pulmonary edema indication may cause treatment to be applied to a patient or result in a modification of a current treatment for the patient. For example, an implanted apparatus may administer a drug to the patient in response to an indication of pulmonary edema. The apparatus may adjust cardiac timing such as V-V timing and A-V timing in response to the indication. The apparatus also may utilize electronic repositioning to reconfigure the electrodes used for therapy.

BRIEF DESCRIPTION OF THE DRAWINGS

These and other features, aspects and advantages of the invention will be more fully understood when considered with respect to the following detailed description, appended claims and accompanying drawings, wherein:

Figure 1:
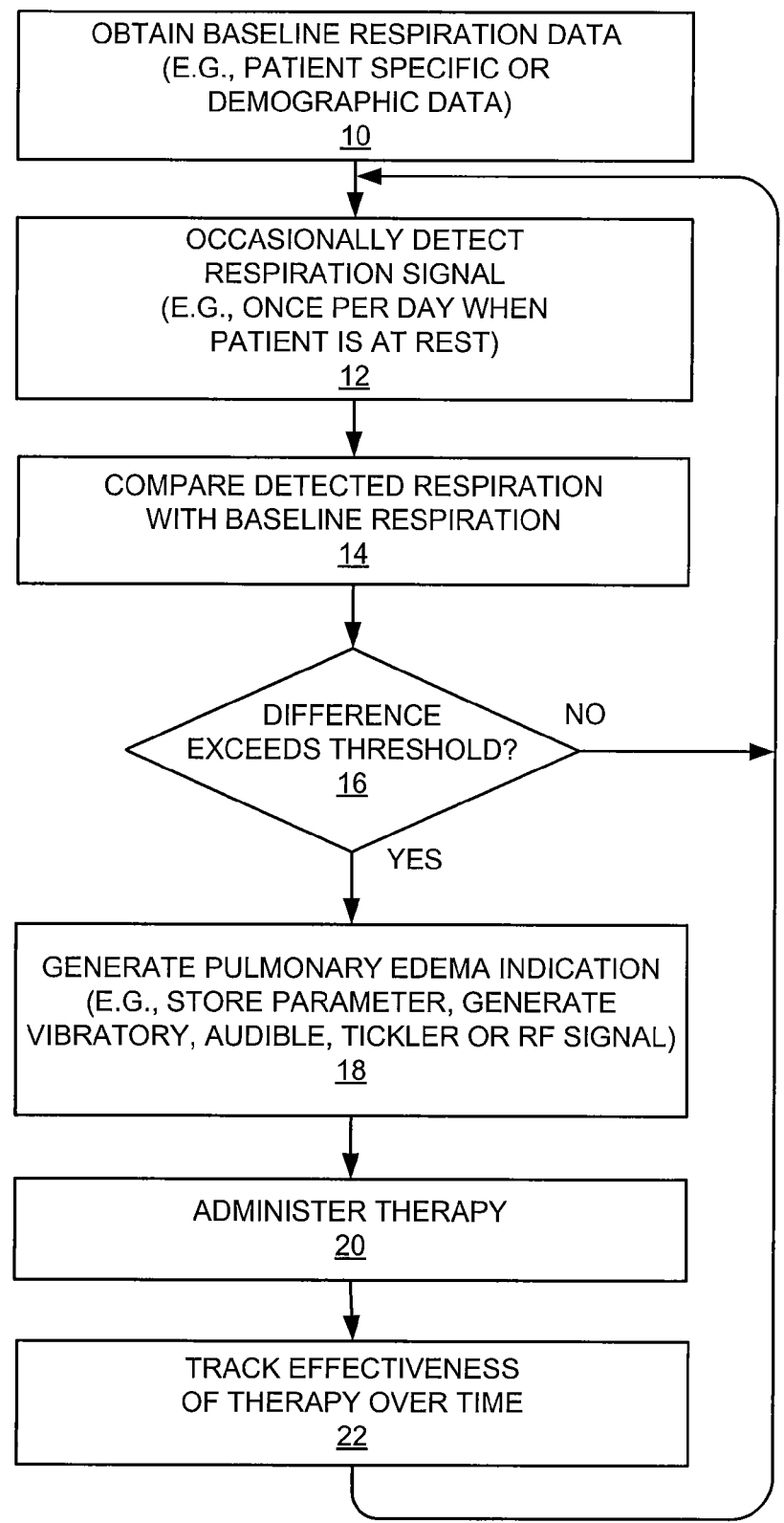
FIG. 1 is a flowchart of an embodiment of operations that may be performed to detect pulmonary edema.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method or precisely depict anatomical features. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s).

FIG. 1 illustrates an embodiment of operations that may be performed to detect pulmonary edema. In general, these operations involve tracking changes in a signal representative of the patient's respiration pattern to identify any changes in the signal that are indicative of pulmonary edema.

As will be discussed in more detail below, these operations may be performed at least in part by an apparatus that is implanted in a patient. Such an apparatus generally includes a signal processing component for detecting and processing a respiration signal. For example, in some embodiments a least a portion of the operations may be performed by an implantable medical device. Such a device may include or may be adapted to couple with a sensing apparatus for sensing the respiration signal. In some embodiments at least a portion of the operations may be performed by an implantable cardiac device. Such a device may, for example, provide cardiac stimulation therapy via one or more implanted cardiac leads. Advantageously, these leads also may be used to sense a respiration signal.

As represented by block 10 of FIG. 1, an initial operation involves obtaining baseline respiration data from the patient. The baseline data is used in subsequent operations to identify any changes in the patient's respiration. Thus, the baseline data may represent the patient's respiration in the absence of pulmonary edema.

In some embodiments the baseline data may be patient specific. For example, the baseline data may be obtained by detecting the patient's respiration pattern and processing the corresponding respiration signal. In practice, the patient's respiration may be detected over several cycles and averaged to provide the respiration signal. In a typical case, the baseline data obtained and stored in the edema monitoring apparatus when the apparatus is initially implanted. It should be appreciated, however, that the baseline data may be obtained at other times (e.g., before or after implant).

Alternatively, in some embodiments the baseline data may comprise data that has not been collected from a specific patient. For example, demographic data representative of normal (e.g., average or mean) values of respiration parameters may be collected from a sampling of a representative group of people. Here, different classes of baseline data may be defined for different types of patients. For example, different classes may be defined based on the cardiac condition of a patient (e.g., heart failure classification), the age of the patient, the patient's sex, the relative health of the patient, or some other suitable parameter(s).

As represented by block 12, occasionally the respiration of the patient is monitored. This operation may be performed, for example, on a regular basis or a periodic basis such as once a day, once a week, etc. In some embodiments the patient's respiration may be repeatedly monitored under similar conditions. For example, monitoring may be conducted at a specific time of day, when the patient is engaged in a particular level of activity, when the patient is in particular position, or under other suitable conditions.

Here, a sensor or some other mechanism may be employed to generate signals representative of the patient's respiration. Again, a respiration signal may be obtained by averaging multiple sensed respiration signals. As will be discussed in more detail below, such a mechanism may, in some embodiments, measure transthoracic impedance to obtain a respiration signal or derive a respiration signal from an IEGM signal.

As represented by block 14, the respiration pattern detected at block 12 is compared with the baseline respiration pattern obtained at block 10. Here, one or more characteristics of the respective respiration patterns may be compared to determine whether there has been a change in a given characteristic. Such characteristics may include, for example, a respiration rate, a magnitude of a respiration signal, a pulse width of a respiration signal, morphology data representative of a respiration signal, or some other suitable characteristic or parameter associated with the patient's respiration. These characteristics may thus be monitored over time to identify any trends in these characteristics and/or to determine whether a magnitude of a characteristic is within an accepted range of values.

As represented by blocks 16 and 18, pulmonary edema may be indicated when the detected respiration signal differs from the baseline respiration signal by a predefined margin. This difference may be quantified through the use of a threshold or some other mechanism. In embodiments that utilize morphology data, a pulmonary edema indication may result from a morphology discrimination score that is below a baseline threshold score.

If the difference at block 16 does not exceed such a threshold or margin, the process returns to block 12 to continue the repetitive monitoring of the patient's respiration.

In contrast, if the difference at block 16 does exceed the threshold or margin a pulmonary edema indication is generated. In some embodiments this may involve one or more of setting a corresponding parameter, generating a warning signal (e.g., a vibratory, audible or tickler signal) or sending an indication to an external device (e.g., via a radio frequency signal). In the latter case, the external device may send a notification to the patient, the patient's physician or some other person or entity via an appropriate communication mechanism (e.g., a telephone system or a data network).

As represented by block 20, in some embodiments therapy may be administered to the patient based on the pulmonary edema indication. For example, therapy (e.g., a drug) may be administered to the patient or a prescribed therapy may be modified. To this end, the implanted apparatus may include a drug delivery mechanism or the implanted apparatus may generate an indication (e.g., a signal) that causes a separate drug delivery mechanism to deliver a drug.

In some embodiments the apparatus may adjust cardiac pacing timing in response to an indication of pulmonary edema. For example, the apparatus may adjust the V-V timing in an attempt to improve cardiac performance. Alternatively or in addition, the apparatus may adjust other timing such as A-V timing.

In some embodiments, in response to a pulmonary edema indication, the apparatus may utilize electronic repositioning to reconfigure the electrodes used for therapy. For example, an implanted cardiac lead may include several electrodes, one or more of which may be selected for providing therapy (e.g., cardiac pacing). Thus, electronic repositioning may involve selecting a particular combination of the electrodes that provides the most effective therapy.

As represented by block 22, the patient's condition may be tracked over time to determine the effectiveness of the therapy being administered to the patient. For example, after a change in therapy the apparatus may store the results of block 14 each time the operation is performed. The apparatus may then analyze the stored data over time to determine, for example, whether the detected respiration is trending back toward the baseline respiration. In this way, the apparatus may track progression of heart failure. If the detected respiration is not trending back to baseline (e.g., within a few days, a few weeks, etc.), the apparatus may generate another indication at block 18 to signal that the patient is not improving. In addition, the apparatus may alter the prescribed therapy as described above in conjunction with block 20 in response to such an indication.

Exemplary Cardiac Device

With the above overview in mind, additional details of pulmonary edema monitoring will be discussed in conjunction with a specific example where monitoring is performed by an implantable cardiac device (e.g., a stimulation device such as an implantable cardioverter defibrillator, a pacemaker, etc.). It should be appreciated that this example is provided for explanatory purposes and that pulmonary edema monitoring may be implemented using other types of devices. It also should be appreciated and understood that other cardiac devices, including those that are not necessarily implantable, may be used in conjunction with the teachings herein.

Figure 2:
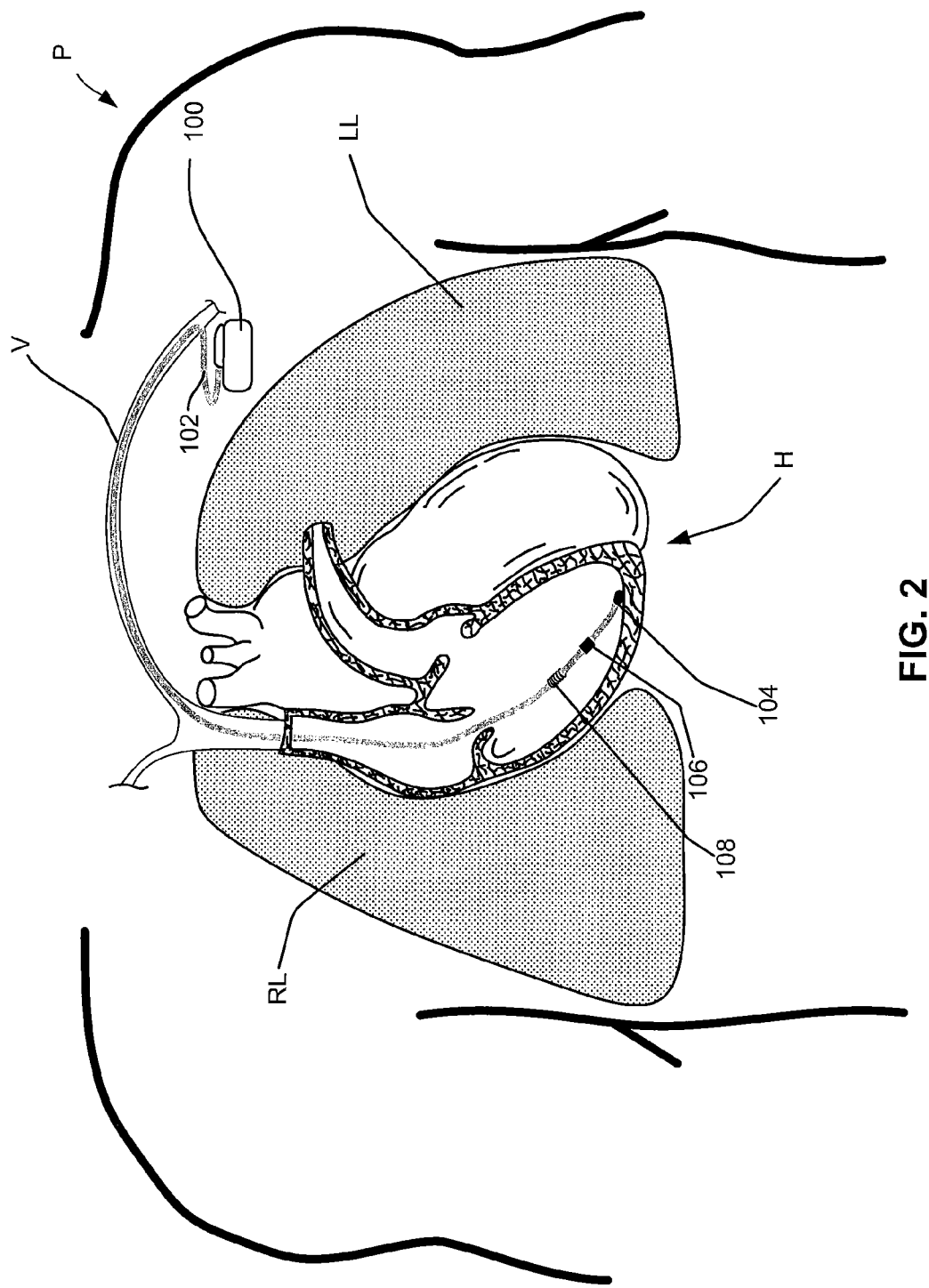
FIG. 2 is a simplified cutaway view of an embodiment of a cardiac device implanted in a patient and in electrical communication with at least one lead implanted in a patient's heart for sensing conditions in the patient and/or delivering therapy to the patient.

FIG. 2 illustrates an exemplary implantable cardiac device 100 in electrical communication with a heart H of a patient P by way of an implantable right ventricular lead 102, suitable for sensing and delivering stimulation (e.g., pacing and shocking) therapy. In this example, the lead 102 includes a right ventricular tip electrode 104, a right ventricular ring electrode 106 and a right ventricular (RV) coil electrode 108. In some embodiments the device 100 also may be in electrical communication with the patient's heart H by way of a superior vena cava (SVC) coil electrode (not shown) on the lead 102.

In the example of FIG. 2, the device 100 is implanted subcutaneously in the pectoral region of the patient P and the right ventricular lead 102 is inserted into a vein V then routed into the heart H. In a typical implementation the lead 102 is configured and implanted to place the right ventricular tip electrode 104 in the right ventricular apex so that the RV coil electrode 108 will be positioned in the right ventricle and an SVC coil electrode will be positioned in the superior vena cava. Accordingly, the right ventricular lead 102 is capable of sensing or receiving cardiac signals, and delivering stimulation in the form of pacing and shock therapy to the heart.

In practice, the device 100 may be coupled to several leads (not shown) to provide multi-chamber sensing and stimulation. For example, to sense atrial cardiac signals and to provide right atrial chamber stimulation therapy, device 100 may be coupled to an implantable right atrial lead (not shown) having, for example, an atrial tip electrode that is typically implanted in the patient's right atrial appendage or septum, and an atrial ring electrode.

To sense left atrial and ventricular cardiac signals and to provide left chamber pacing therapy, device 100 may be coupled to a coronary sinus lead (not shown) designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

An exemplary coronary sinus lead may be designed to receive atrial and ventricular cardiac signals and to deliver left ventricular pacing therapy using, for example, a left ventricular tip electrode and, optionally, a left ventricular ring electrode; provide left atrial pacing therapy using, for example, a left atrial ring electrode; and provide shocking therapy using, for example, a left atrial coil electrode. For a more detailed description of a coronary sinus lead, the reader is directed to U.S. Pat. No. 5,466,254, "Coronary Sinus Lead with Atrial Sensing Capability" (Helland), which is incorporated herein by reference.

It should thus be appreciated that the device 100 may be coupled to various types of leads other than those specifically shown or described herein. In addition, a lead may be implanted using various techniques and at various locations. For example, a lead may be positioned in, near or remote from the heart.

Also, while FIG. 1 illustrates an endocardial lead, the device 100 may be used in conjunction with an epicardial lead, a pericardial lead or another lead implanted in some other suitable manner. In particular, a lead used for detecting pulmonary edema may be implanted in any manner (e.g., anywhere in the body) that provides a suitable vector for acquiring a patient's respiration pattern.

A lead connected to the device 100 may include components other than those shown in FIG. 2. For example, a lead may include other types of electrodes, sensors (e.g., a physiologic sensor) or devices that serve to otherwise interact with a patient or the surroundings.

Figure 3:
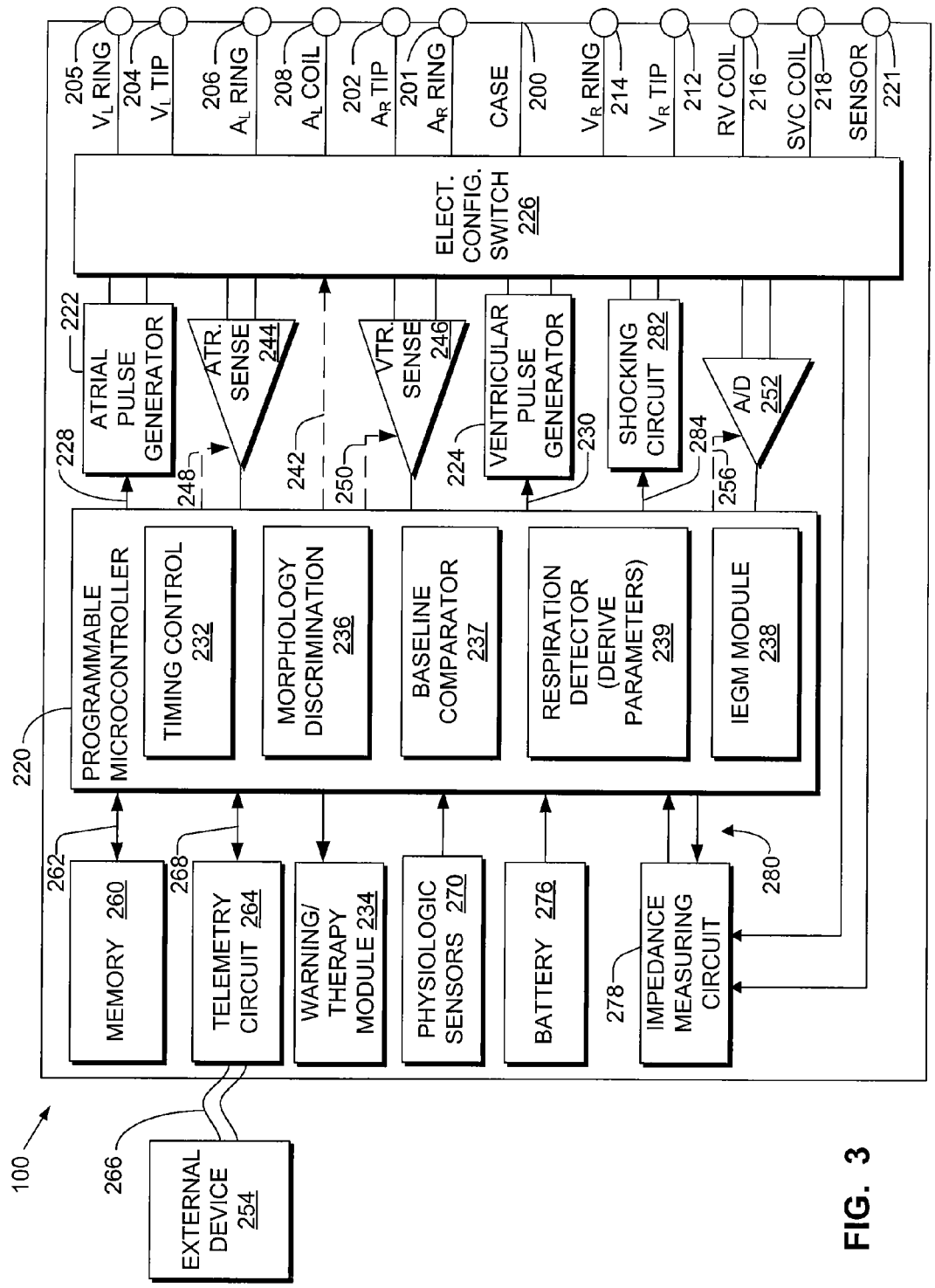
FIG. 3 is a simplified functional block diagram of an embodiment of implantable cardiac device, illustrating basic elements that may be configured to sense conditions in the patient and deliver therapy to the patient.

FIG. 3 is an exemplary, simplified block diagram depicting various components of a cardiac device 100. The device 100 may be adapted to treat both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described herein may be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 200 for device 100 is often referred to as the "can", "case" or "case electrode", and may be programmably selected to act as the return electrode for all "unipolar" modes. Housing 200 may further be used as a return electrode alone or in combination with one or more of the coil electrodes (e.g., electrode 108) for shocking purposes. Housing 200 further includes a connector (not shown) having a plurality of terminals 201, 202, 204, 205, 206, 208, 212, 214, 216 and 218 (shown schematically and, for convenience, the names of the electrodes to which they are connected are shown next to the terminals). The connector may be configured to include various other terminals depending on the requirements of a given application. For example, in some embodiments the connector may include one or more terminals 221 that connect to one or more external sensors (not shown).

To achieve right atrial sensing and pacing, the connector includes, for example, a right atrial tip terminal (AR TIP) 202 adapted for connection to an atrial tip electrode. A right atrial ring terminal (AR RING) 201 may also be included and adapted for connection to an atrial ring electrode. To achieve left chamber sensing, pacing, and shocking, the connector includes, for example, a left ventricular tip terminal (VL TIP) 204, a left ventricular ring terminal (VL RING) 205, a left atrial ring terminal (AL RING) 206, and a left atrial shocking terminal (AL COIL) 208, which are adapted for connection to a left ventricular tip electrode, a left ventricular ring electrode, a left atrial ring electrode, and a left atrial coil electrode, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 104, the right ventricular ring electrode 106, the RV coil electrode 108, and an SVC coil electrode, respectively.

At the core of the device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller (e.g., a signal processor) or other processing component(s) may be used for carrying out the functions described herein. The use of microprocessor-based control circuits for performing timing and data analysis functions are well known in the art.

Representative types of control circuitry that may be used in connection with the described embodiments may include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device 100 and their inter-relationship, see U.S. Pat. No. 4,788,980 (Mann et al.), also incorporated herein by reference.

FIG. 3 also shows an atrial pulse generator 222 and a ventricular pulse generator 224 that generate pacing stimulation pulses for delivery by a right atrial lead, a coronary sinus lead, and/or the right ventricular lead 102 via an electrode configuration switch 226. It is understood that in order to provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 (e.g., implementing one or more timers) to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, or other time periods, as is known in the art.

Microcontroller 220 further includes an arrhythmia detector (not shown). The arrhythmia detector may be utilized by the device 100 for determining desirable times to administer various therapies. The arrhythmia detector may be implemented, for example, in hardware as part of the microcontroller 220 and/or as software/firmware instructions programmed into the device and executed on the microcontroller 220 during certain modes of operation.

Microcontroller 220 may include a morphology discrimination module 236, a capture detection module (not shown) and an auto sensing module (not shown). These modules are optionally used to implement various exemplary recognition algorithms and/or methods. The aforementioned components may be implemented, for example, in hardware as part of the microcontroller 220 and/or as software/firmware instructions programmed into the device and executed on the microcontroller 220 during certain modes of operation.

The electrode configuration switch 226 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 226, in response to a control signal 242 from the microcontroller 220, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 244 and ventricular sensing circuits (VTR. SENSE) 246 may also be selectively coupled to a right atrial lead, a coronary sinus lead, and the right ventricular lead 102, through the switch 226 for detecting the presence of cardiac activity in each of the four chambers of the heart. Accordingly, the atrial and ventricular sensing circuits 244 and 246 may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., circuits 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or a data acquisition system 252. This information may be used to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits 244 and 246 as is known in the art.

For arrhythmia detection, the device 100 utilizes the atrial and ventricular sensing circuits 244 and 246 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector of the microcontroller 220 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 252. The data acquisition system 252 is configured (e.g., via signal line 256) to acquire analog signals, convert the raw analog signals into a digital signal, and store the digital signals for later processing and/or telemetric transmission to an external device 254. For example, the data acquisition system 252 may be coupled to a right atrial lead, a coronary sinus lead, the right ventricular lead 102 and other leads through the switch 226 to sample cardiac signals across any pair of desired electrodes.

The data acquisition system 252 also may be coupled to receive signals from other input devices. For example, the data acquisition system 252 may sample signals from leads or other components (e.g., via terminal 221, etc.) coupled to the switch 226. In addition, the data acquisition system 252 may sample signals from a physiologic sensor 270 or other components shown in FIG. 3 (connections not shown).

Typically, the data acquisition system 252 is configured (e.g., via signal line 256) to acquire intracardiac electrogram ("IEGM") signals. For example, as discussed above, one or more of the leads implanted in the heart H may sense cardiac electrical signals. These signals may thus be coupled to the data acquisition system 252 via the switch 226. As will be discussed in more detail below, the raw IEGM signal data may be provided to an IEGM module 238 for processing.

The microcontroller 220 is further coupled to a memory 260 by a suitable data/address bus 262, wherein the programmable operating parameters used by the microcontroller 220 are stored and modified, as required, in order to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 252), which data may then be used for subsequent analysis to guide the programming of the device or for other operations.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, a diagnostic system analyzer or some other device. The microcontroller 220 activates the telemetry circuit 264 with a control signal (e.g., via bus 268). The telemetry circuit 264 advantageously allows intracardiac electrograms and status information relating to the operation of the device 100 (as contained in the microcontroller 220 or memory 260) to be sent to the external device 254 through an established communication link 266.

The device 100 can further include one or more physiologic sensors 270. In some embodiments the device 100 may include a "rate-responsive" sensor that may provide, for example, information to aid in adjustment of pacing stimulation rate according to the exercise state of the patient. One or more physiologic sensors 270 (e.g., a pressure sensor) may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators 222 and 224 generate stimulation pulses.

While shown as being included within the device 100, it is to be understood that a physiologic sensor 270 may also be external to the device 100, yet still be implanted within or carried by the patient. Examples of physiologic sensors that may be implemented in conjunction with device 100 include sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 270 may optionally include sensors to help detect movement (via, e.g., a position sensor) and/or minute ventilation (via an MV sensor) in the patient. Signals generated by the position sensor and MV sensor may be passed to the microcontroller 220 for analysis in determining whether to adjust the pacing rate, etc. The microcontroller 220 may thus monitor the signals for indications of the patient's position and activity status, such as whether the patient is climbing up stairs or descending down stairs or whether the patient is sitting up after lying down.

The device 100 additionally includes a battery 276 that provides operating power to all of the circuits shown in FIG. 3. For a device 100 which employs shocking therapy, the battery 276 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or other suitable battery technology.

The device 100 can further include magnet detection circuitry (not shown), coupled to the microcontroller 220, to detect when a magnet is placed over the device 100. A magnet may be used by a clinician to perform various test functions of the device 100 and/or to signal the microcontroller 220 that the external device 254 is in place to receive data from or transmit data to the microcontroller 220 through the telemetry circuit 264.

The device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 100 has been implanted; measuring stroke volume; and detecting the opening of heart valves, etc. The impedance measuring circuit 278 is advantageously coupled to the switch 226 so that any desired electrode may be used.

In the case where the device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart H through, for example, two shocking electrodes and as shown in this embodiment, selected from a left atrial coil electrode, an RV coil electrode 108, and/or an SVC coil electrode. As noted above, the housing 200 may act as an active electrode in combination with the RV coil electrode 108, and/or as part of a split electrical vector using the SVC coil electrode or the left atrial coil electrode (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Pulmonary Edema Monitoring

The device 100 also includes several components that provide functionality relating to monitoring pulmonary edema. For example, the microcontroller 220 (e.g., incorporating signal processing functionality) may include an IEGM module 238 adapted to provide an IEGM signal. The microcontroller 220 may include a respiration detector module 239 adapted to generate a respiration signal and derive parameters from the respiration signal. The microcontroller 220 may include a baseline comparator 237 adapted to compare detected signals or parameters with baseline signals or parameters. The device 100 also may include a warning/therapy module 234 adapted to generate warning signals and/or administer therapy. These and other components described herein may be incorporated into an implantable medical device (e.g., a monitoring device), an implantable cardiac device (e.g., a cardiac stimulation device) or any other suitable device in accordance with the requirements of a given application. For convenience, such a device may be referred to in the following discussion simply as "device 100." It should be appreciated, however, that the components and operations described below may be incorporated into any suitable device or combination of devices.

Figure 4:
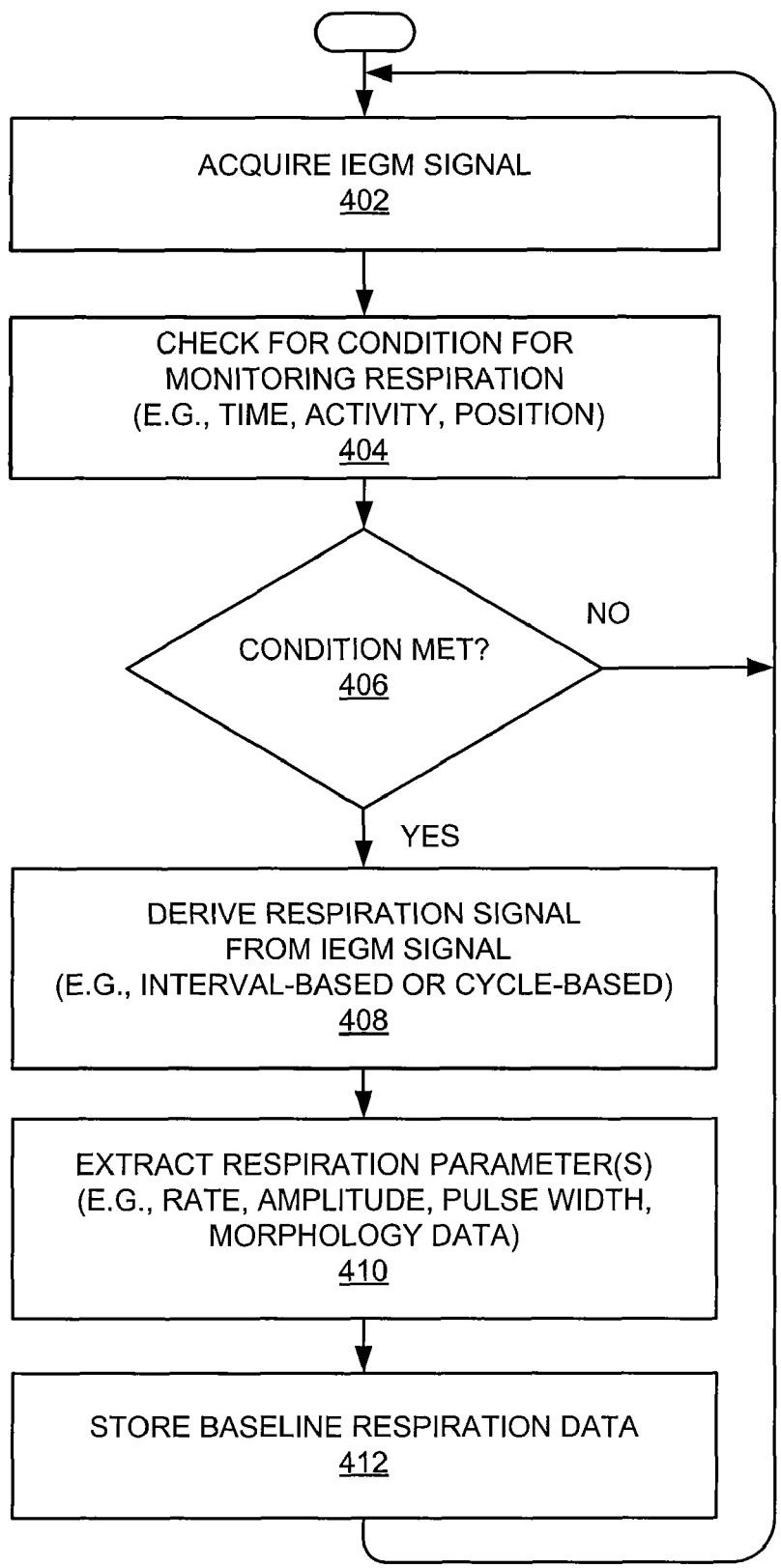
FIG. 4 is a flowchart of an embodiment of operations that may be performed to acquire baseline respiration data.
Figure 5:
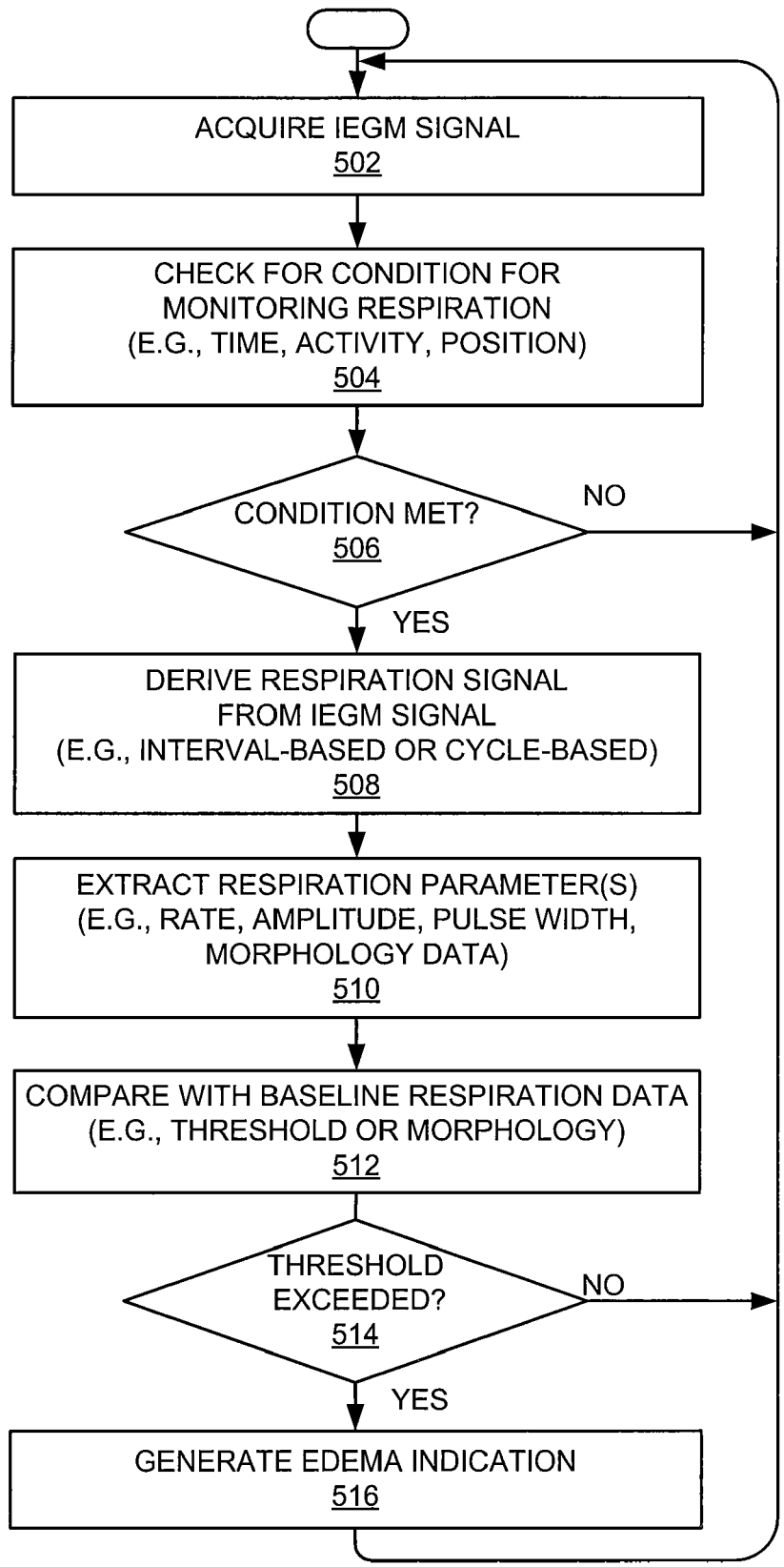
FIG. 5 is a flowchart of an embodiment of operations that may be performed to generate an indication of pulmonary edema.
Figure 6:
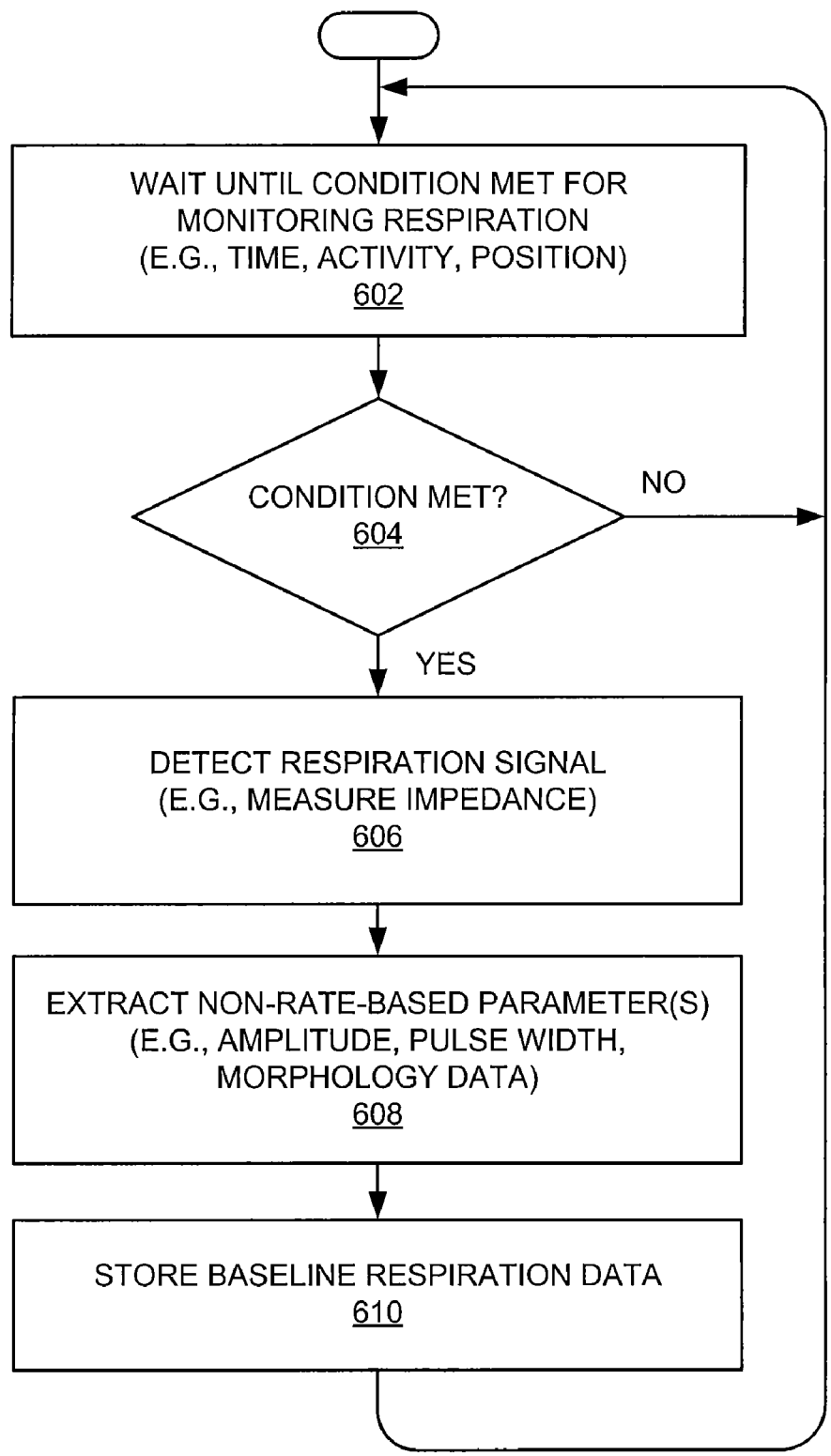
FIG. 6 is a flowchart of an embodiment of operations that may be performed to acquire baseline respiration data.
Figure 7:
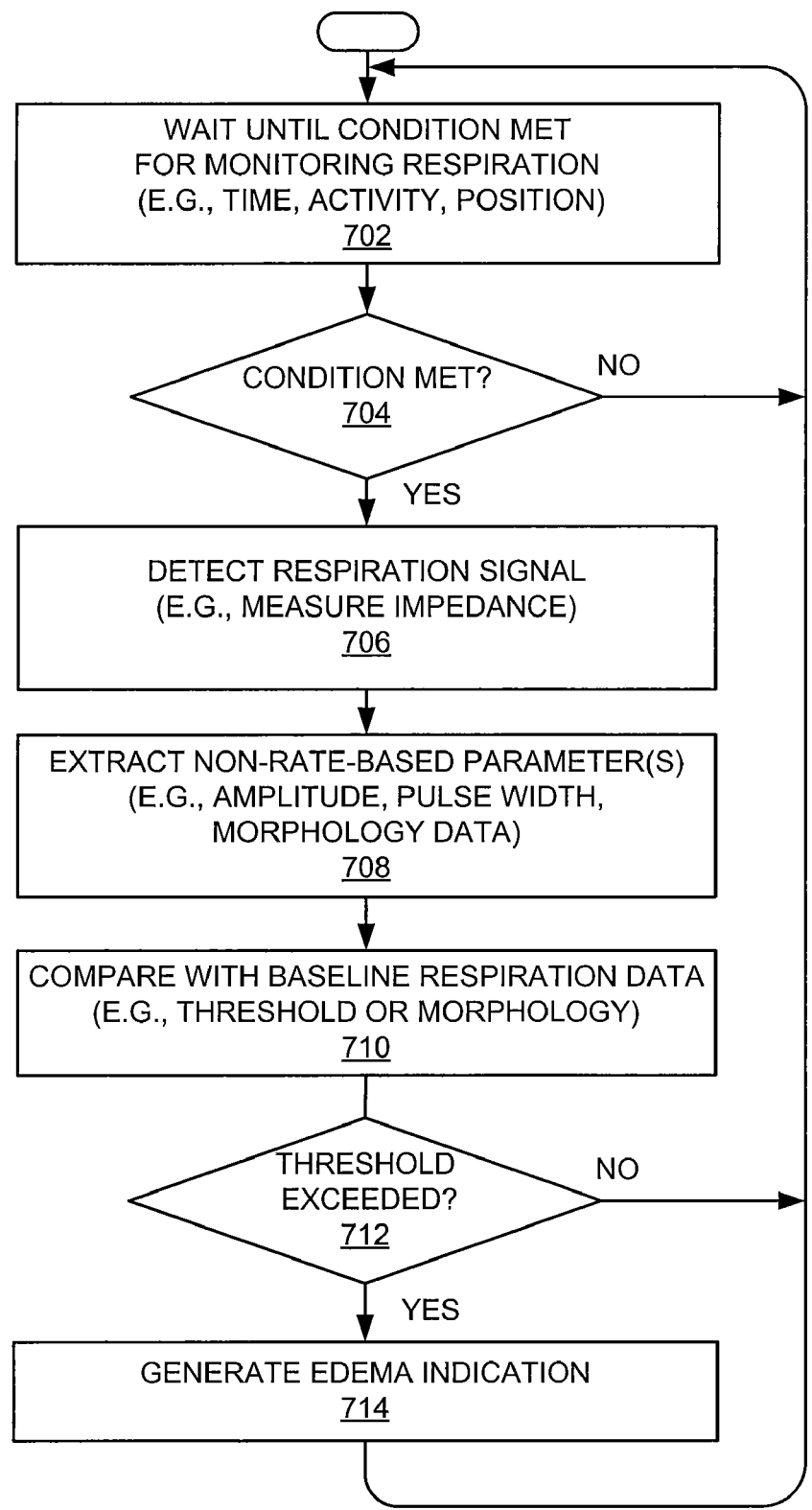
FIG. 7 is a flowchart of an embodiment of operations that may be performed to generate an indication of pulmonary edema.
Figure 8:
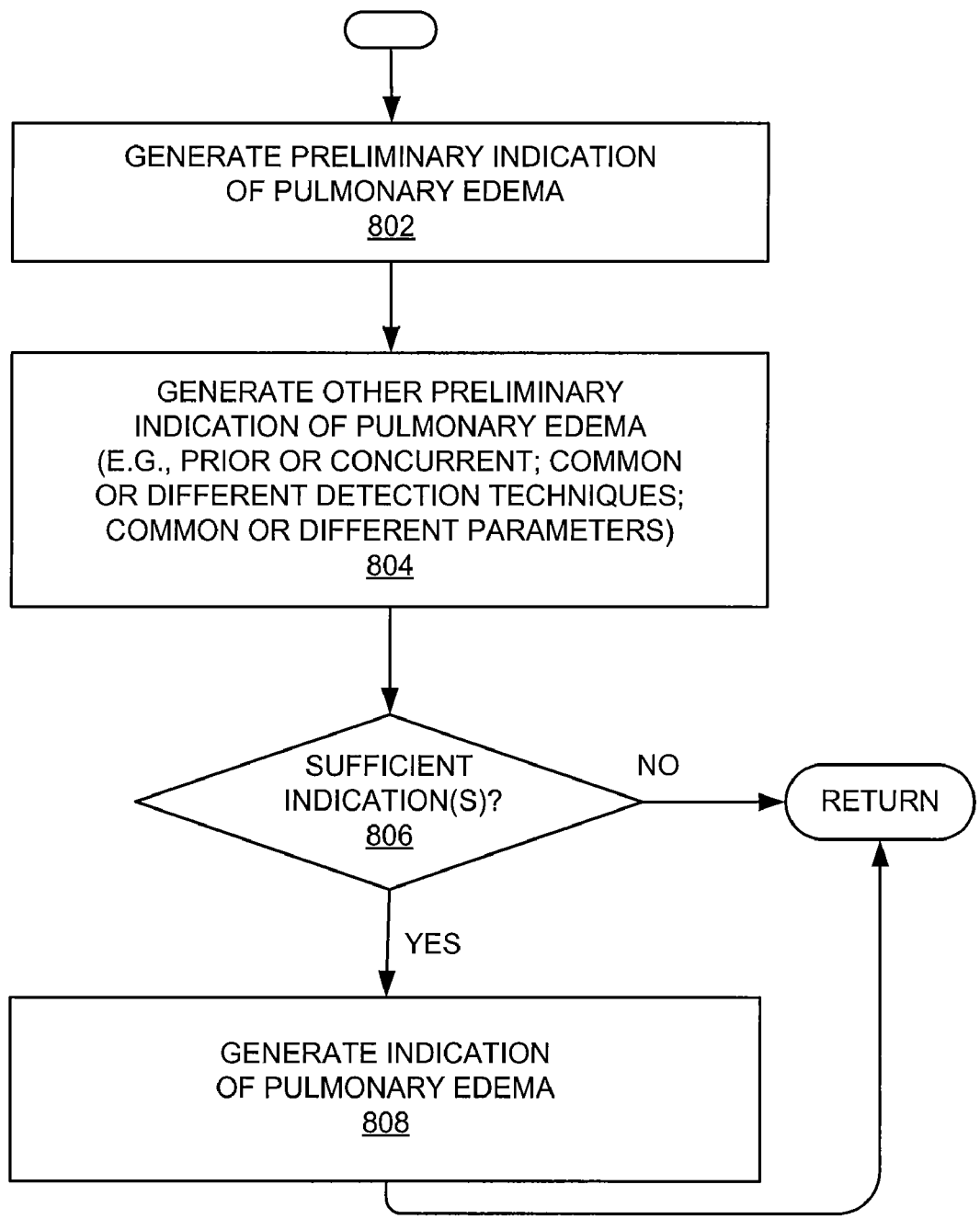
FIG. 8 is a flowchart of an embodiment of operations that may be performed to generate an indication of pulmonary edema based on one or more preliminary pulmonary edema indications.

Exemplary operations of these components and other operations will now be discussed in more detail in conjunction with the flowcharts of FIGS. 4-8. FIG. 4 relates to operations that may be used to create baseline respiration data for embodiments that derive a respiration signal from an IEGM signal. FIG. 5 relates to operations that may be used to generate a pulmonary edema indication through analysis of a respiration signal derived from an IEGM signal. FIG. 6 relates to operations that may be used to create baseline respiration data for embodiments that utilize non-rate-based parameters of a respiration signal to generate a pulmonary edema indication. FIG. 7 relates to operations that may be used to derive a pulmonary edema indication from non-rate based parameters of a respiration signal. FIG. 8 relates to operations that may be used to generate a pulmonary edema indication from one or more preliminary indications of pulmonary edema. For convenience, the operations of FIGS. 4-8 may be described in conjunction with specific embodiments and/or components described herein. It should be appreciated, however, that these operations may be performed in conjunction with or using other components.

Referring to FIG. 4, several operations relating to obtaining baseline data will now be treated. As discussed above, baseline data for the device 100 may be non-patient specific or patient specific. In the former case, a physician may simply store the baseline data in a data memory 260 of the device 100. In a typical case, the physician will program the device 100 in this manner upon implant. It should be appreciated, however, that this data may be updated at any time via the telemetry circuit 264. This approach may have an advantage in that a shorter implant procedure may be required given that the physician will not need to configure or operate the device 100 to acquire patient specific data.

In the latter case, patient specific baseline data may be acquired via the device 100 or some other device (e.g., an external device). For example, a device may be coupled to sensors such that the device may acquire a respiratory signal representative of the respiration pattern of the patient. Such a device may be adapted to process the respiration signal to obtain the desired baseline respiration data.

The specific baseline data acquired at this stage will depend on the techniques that are used to detect pulmonary edema from a respiration signal. Several examples are set forth in the discussion below.

FIG. 4 relates to an embodiment where the device 100 acquires patient-specific baseline data. In particular, FIG. 4 relates to an embodiment where a respiration signal is derived from an IEGM signal. As represented by block 402, the device 100 acquires the IEGM signal by sensing cardiac electrical activity. This may be accomplished through the use of one or more implanted cardiac leads as discussed above (e.g., lead 102 in FIG. 2) or any other suitable lead or mechanism. In the example of FIG. 2, the cardiac signals may be sensed by electrodes 104 and/or electrode 106. The data acquisition system 252 may then digitize the cardiac signals and provide the digitized signals to the IEGM module 238 for further processing.

In embodiments where the device 100 is an implantable cardiac device, the device 100 is typically configured to collect IEGM data on a regular basis for use in cardiac stimulation operations. Accordingly, in such a device 100 the IEGM data is readily available for use in pulmonary edema detection operations. In other words, separate sensing circuitry (e.g., leads, electrodes, or other sensors) may not be needed to provide pulmonary edema detection functionality.

As represented by block 404, the device 100 may be adapted to collect baseline data under a specific condition. For example, the device 100 may collect baseline data at a certain time of day, when the patient is engaged in a particular level of activity (e.g., resting), when the patient is in a particular position (e.g., lying down), or under any other desired conditions. In this way, any subsequent collection of data relating to the patient's respiration may be performed under the same or similar condition(s) as the collection of the baseline data. In some embodiments a specified condition may include one or more of these conditions and/or other suitable conditions.

To detect the current condition, the device 100 includes or is coupled to one or more sensors or other components. For example, the timing control module 232 may include a timer for generating time of day information. In addition, a physiologic sensor 270 and/or a sensor connected to terminal 221 may comprises an accelerometer, a position sensor or some other type of sensor suitable for determining the activity level or position of the patient.

As represented by block 406, if the specified condition in not met the device 100 will wait to collect the baseline data until the condition is met. On the other hand, if the condition is met the device 100 (e.g., module 239) derives the respiration signal from the IEGM signal (block 408).

Various techniques may be used to derive a respiration signal from an IEGM signal. For example, in some embodiments the device 100 derives the respiration signal by detecting changes in interval-based features associated with the IEGM signal. In other embodiments the device 100 derives a respiration signal by detecting cycle-to-cycle changes in individual morphological features associated with the IEGM signal. Several examples of these techniques will be described in more detail in conjunction with FIG. 5.

As represented by block 410, the device 100 may then detect one or more morphological parameters associated with the derived respiration signal. Such parameters may include, for example, one or more of: the respiration rate, an amplitude associated with the respiration signal, or a pulse width associated with the respiration signal. In addition, as mentioned above the parameter also may comprise morphology data. In this case, the baseline data may comprise a baseline morphology template representative of the respiration signal.

As represented by block 412, the device 100 (e.g., module 239) may store the parameter(s). In the example of FIG. 3 the parameter(s) may thus be stored in the data memory 260.

An embodiment that incorporates the operations of FIG. 4 may advantageously provide dynamic baseline data. As an example, the baseline data may be updated as necessary to better reflect the normal respiration of the patient in the event the normal respiration of the patient changes. Such adaptation may be desirable, for example, in the event the patient's health changes due to a condition other than pulmonary edema and that change in health effects the patient's normal respiration.

Referring now to FIG. 5, an embodiment of operations that may be performed to generate a pulmonary edema indication based on a respiration signal derived from an IEGM signal will be treated. These operations may be performed on a relatively regular basis (e.g., daily) over a relatively long period of time (e.g., years). In this way, the device 100 may identify pulmonary edema at an early stage to thereby safeguard the health of the patient and prevent the need for hospitalization that may be required in the event the pulmonary edema is not detected at an early stage.

At block 502, the device 100 acquires the IEGM signal. In general, this operation may be similar to the operation described above in conjunction with block 402. For example, an implantable cardiac device 100 may acquire the IEGM signal in conjunction with its cardiac stimulation operations.

At blocks 504 and 506, the device 100 may process IEGM signals collected under a specified condition. For example, as discussed above in conjunction with blocks 404 and 406, the device 100 may process the IEGM signals that were collected at a specific time of day, when the patient was engaged in a specified level of activity, or when the patient was in a particular position. Again, in some embodiments a specified condition may include one or more of these conditions and/or other suitable conditions. If the specified condition is not met at block 506, the device 100 will instead process IEGM signals collected at a time when the condition is met.

If, at block 506, the condition is met, the device 100 (e.g., module 239) derives the respiration signal from the IEGM signal (block 508). Various techniques may be used to derive a respiration signal from an IEGM signal. Several examples follow.

One form of technique for deriving respiration from an IEGM signal relates to detecting cycle-to-cycle changes in individual morphological features associated with the IEGM signal. For example, the device 100 may sense IEGM signals and identify individual cardiac cycles therein. The device 100 may then identify selected individual electrical events, such as depolarization events (e.g., P-waves, QRS-complexes, atrial evoked responses, ventricular evoked responses) or repolarization events (e.g., T-waves) within the cardiac cycles.

The device 100 also may detect one or more morphological parameters associated with the individual features. Such parameters may include, for example, a maximum amplitude of the IEGM signal, a peak-to-peak amplitude of the IEGM signal, or a numerical integral such as paced depolarization integral. In one specific example, changes in the integrals of the QRS-complex derived from a V-IEGM ("V-IEGM") channel signal are examined, alone or in combination with, integrals of P-waves derived from an atrial IEGM ("A-IEGM") channel signal.

The device 100 may thus detect patient respiration based on cycle-to-cycle changes in the detected parameters associated with the individual selected electrical events. In other words, this technique may involve examining changes within individual features of cardiac cycles over time. In this regard, it has been observed that respiration causes slight variations in the size and shape of individual electrical events of the IEGM signals, such as QRS-complexes, and that those changes are correlated with respiration.

Otherwise conventional filters may be used to isolate cyclical patterns appearing at frequencies associated with respiration. Additionally, an analysis of changes in the intervals between beats (e.g., interval-based parameters, such as variations in A-A, R-R or AV intervals) may be used to enhance the reliability of the respiration detection technique of step 508. In other words, both interval-based and individual feature-based techniques may be employed to enhance detection specificity.

One example of an interval-based technique for deriving a respiration signal from an IEGM signal is described in U.S. Pat. No. 6,697,672 ("Andersson"), the disclosure of which is incorporated by reference herein. Briefly, Andersson describes a technique for extracting parameters related to patient respiration via analysis of intervals between various events detected within a V-IEGM signal. For example, cycle-to-cycle variability is tracked in R-R intervals or in the amplitude of S-T intervals. In other words, the technique of Andersson exploits interval-based morphological features of the V-IEGM to track respiration.

Other interval-based techniques may be employed to derive a respiration signal from an IEGM signal. For example, intervals between successive beats (or between successive features of an individual beat) may generally be employed to derive a respiration signal. Here, the device 100 may sense A-IEGM and/or V-IEGM signals and detect sequences of consecutive P-waves and/or R-waves within the IEGM signal. Next, the device 100 calculates selected intervals, e.g., A-A intervals, AV intervals or R-R intervals. A-A intervals, which represent the intervals between consecutive P-waves, are preferably derived from an A-IEGM signal; whereas R-R intervals, which represent the intervals between consecutive QRS-complexes, are preferably derived from a V-IEGM signal. As alluded to above, the device 100 may calculate these intervals as part of its routine operations.

The device 100 then tracks changes in the intervals from cycle-to-cycle and derives respiration from changes in the intervals over time, typically, over at least a few dozen cardiac cycles. For example, a given interval value, such as an A-A interval derived from an A-IEGM signal, may be calculated between each successive pair of P-waves, with the value of the interval then plotted as a function of time or as a function of cardiac cycle number so as to track the cyclical features of respiration.

Accordingly, this technique may be based on either A-IEGM or V-IEGM signals, and may further be based on A-A intervals, AV intervals, R-R intervals, R-ST intervals or some combination thereof. Unipolar or Bipolar signals may be employed, as well as cross-chamber signals. The respiration patterns derived from cycle-to-cycle changes in intervals may be merged with respiration patterns derived from depolarization events or repolarization events, described above, to provide further specificity.

In practice, the respiration patterns derived as discussed above may not precisely approximate the actual smooth respiration patterns of patient. Nevertheless the derived patterns may provide sufficient information from which respiration rate, relative amplitude and other parameters may be derived.

For convenience, the above techniques for tracking respiration via an IEGM signal have been described with reference to the device 100. It should be appreciated, however, that the teachings herein may be implemented within other devices. For example, the teachings herein may be applicable to detecting respiration via surface EKG signals and hence are not necessarily limited to use with implantable devices. In this regard, it is known that the mean cardiac axis and EKG morphology is influenced by electrode motion relative to the heart and by changes in thoracic electrical impedance as the lungs fill and empty. The sinus rate is modulated by vagal influences in synchronization with respiration. Pressure changes (i.e. breathing-related as well as cardiac cycle-related pressure changes) also influence IEGM morphology.

Referring again to FIG. 5, at block 510 the device 100 extracts one or more parameters from the derived respiration signal to facilitate tracking changes in the derived respiration signal. These parameters may include, for example, the respiration rate, the amplitude of the respiration signal, the pulse width of the patient's breaths, morphology data representative of the respiration signal, or some other suitable parameter.

At block 512 the device 100 (e.g., baseline comparator 237 and/or morphology discrimination module 236) compares the parameter or parameters extracted at block 510 with corresponding baseline parameters. For example, the extracted data may be compared with the baseline respiration data stored in the data memory 260 in conjunction with block 412 discussed above.

As represented by blocks 514 and 516, the device may generate a pulmonary edema indication depending upon the relative values of the extracted parameter and the baseline parameter. For example, in some embodiments a deviation on the order of 20% to 50% may indicate a pulmonary edema condition. Here, since a patient suffering from pulmonary edema may have shortness of breath, the respiration pattern may show changes in one or more of respiration rate, amplitude, pulse width, etc. In particular, there may be an increase in the respiration rate, a decrease in the amplitude, a decrease in the pulse width, or some combination of these changes.

It should be appreciated that the magnitude of the threshold may depend on the particular parameters being compared. For example, pulmonary edema may cause a larger percentage change in the width of a breath as opposed to the percentage change in the amplitude of the respiration signal.

As mentioned above, the parameter also may comprise morphology data. In this case, a morphology discrimination module 236 (FIG. 3) may perform a cross-correlation operation on the derived morphology data and the baseline morphology template discussed above in conjunction with FIG. 4. Here, a morphology discrimination score on the order of, for example, 0.8 or less may indicate a pulmonary edema condition.

As discussed above, generation of the indication may comprise, relate to or cause the invocation of various operations. For example, in some embodiments the device 100 stores an associated parameter in the data memory 260. In some embodiments a warning/therapy module 234 may generate an appropriate warning signal (e.g., via an actuator) such as an audible signal or a vibratory signal. In some embodiments the warning/therapy module 234 may generate a tissue tickler warning signal by, for example, applying an electrical signal to tissue in the patient's body via an electrode. Alternatively or additionally, an appropriate indication may be transmitted to an external apparatus via the telemetry circuit 264. In addition, in some embodiments the warning/therapy module 234 may administer or modify a therapy as discussed above.

Referring now to FIGS. 6 and 7, in some embodiments the device 100 may generate a pulmonary edema indication based on non-rate-based parameters extracted from a respiration signal. Here, the respiration signal may be derived using any known technique including, for example, impedance measurements, the IEGM-based technique discussed above, etc.

FIG. 6 relates to an embodiment where the device 100 acquires patient-specific baseline data. Blocks 602 and 604 represent operations where the device 100 is adapted to collect baseline data under a specific condition as discussed above. Again, the device 100 may collect baseline data at a certain time of day, when the patient is engaged in a particular level of activity (e.g., resting), when the patient is in a particular position (e.g., lying down), or under any other desired conditions. In addition, a specified condition may include one or more of these conditions and/or other suitable conditions.

As represented by block 606, the device 100 detects the respiration signal using an impedance technique, an IEGM-based technique as discussed above or some other suitable technique. One form of impedance technique derives a respiration signal by measuring transthoracic impedance. This may be accomplished through the use of one or more implanted leads as discussed herein (e.g., lead 102 in FIG. 2) or any other suitable lead or mechanism. In the example shown in FIG. 2, the impedance may be measured by sending a signal (e.g., a series of short pulses) between the case electrode and one or more of the electrodes 104 and 106. In this way, the impedance path may include at least a portion of the right lung ("RL") and at least a portion of the left lung ("LL"). Consequently, as air moves into and out of the lungs RL and LL when the patient P breaths, the measured impedance will change. The signals sensed by the electrodes may then be coupled to the impedance measuring circuit 278 via the switch 226.

At block 608 the device 100 (e.g., module 239) extracts one or more non-rate-based parameters from the detected respiration signal. Such a parameter may comprise, for example, an amplitude associated with the respiration signal, or a pulse width associated with the respiration signal. In addition, as mentioned above the parameter may comprise morphology data. In this case, the baseline data may comprise a baseline morphology template representative of the respiration signal. The device may then store the parameter(s) in the data memory 260 (block 610).

Referring now to FIG. 7, an embodiment of operations that may be performed to generate a pulmonary edema indication based on non-rate-based parameters extracted from a respiration signal will be treated. Again, these operations may be performed on a relatively regular basis (e.g., daily) over a relatively long period of time (e.g., years) to identify pulmonary edema at an early stage.

As represented by blocks 702 and 704, the device 100 may detect the respiration signal only when a specified condition is satisfied. For example, as discussed above in conjunction with blocks 602 and 604, the device 100 may monitor respiration at a specific time of day, when the patient is engaged in a specified level of activity, or when the patient is in a particular position. Again, a specified condition may include one or more of these conditions and/or other suitable conditions. If the specified condition is not met at block 704, the device 100 will wait to detect the respiration signal at a later time when the specified condition is met.

If, at block 704, the condition is met, the device 100 (e.g., circuit 278) detects the respiration signal (block 706). This operation may be similar to the operation discussed above in conjunction with block 606.

At block 708 the device 100 (e.g., module 239) extracts non-rate-based parameters from the respiration signal. This operation may be similar to the operation discussed above in conjunction with block 608. Consequently, the device 100 may extract parameters such as an amplitude associated with the respiration signal, a pulse width associated with the respiration signal and morphology data from the respiration signal.

At block 710 the device 100 (e.g., baseline comparator 237 and/or morphology discrimination module 236) compares each parameter extracted at block 708 with a corresponding baseline parameter. For example, extracted data may be compared with the baseline respiration data stored in the data memory 260 in conjunction with block 610 discussed above.

As represented by blocks 712 and 714, the device 100 may generate a pulmonary edema indication depending upon the relative values of the extracted parameter and the baseline parameter. Again, based on the indication, in some embodiments the warning/therapy module 234 may generate an appropriate warning and/or administer or modify a therapy.

Referring to FIG. 8, in some embodiments a pulmonary edema indication as discussed herein may be used as a preliminary indication of pulmonary edema. In this way, one preliminary indication (block 802) may be used in conjunction with another preliminary indication (block 804) or some condition or event to provide a higher degree of certainty as to whether a pulmonary edema condition exists. For example, a combination of indications may tend to eliminate spurious false positives or provide a way to factor out other conditions that may affect a respiration signal (e.g., a cold).

Here, a combination of preliminary indications may involve indications that were generated concurrently or at different times. For example, preliminary indications generated using a common technique may be generated at different times.

Alternatively, preliminary indications generated using different techniques may be generated concurrently or at different times. For example, one indication may be based on an impedance-derived respiration signal while another concurrently generated indication is based on an IEGM-based respiration signal.

A combination also may involve indications that are based on common or different parameters. For example, one indication may be based on an amplitude of a respiration signal while another indication is based on a pulse width of a respiration signal.

In some embodiments, generation of a pulmonary edema indication may be conditioned upon an indication of heart failure in a patient. As an example, the pulmonary edema monitoring may be enabled upon detection of conditions (e.g., via appropriate sensors or other techniques) that indicate the patient is suffering from, for example, progressive heart failure (e.g., by monitoring the QRS complex or left atrial pressure).

As represented by blocks 806 and 808, in the event the device 100 determines that the indication or indications is/are sufficient to indicate pulmonary edema, the device 100 may generate a final indication of pulmonary edema.

It should be appreciated that various modifications may be incorporated into the disclosed embodiments based on the teachings herein. For example, the structure and functionality taught herein may be incorporated into different types of devices other than those types specifically described. In addition, the various signals described herein and/or other signals may be sensed in other ways and using different sensing components. Such sensors (e.g., electrodes, physiologic sensors, etc.) also may be incorporated into other types of implantable leads or may be implanted or otherwise provided without the use of leads. These sensors may be located at various positions throughout the heart or the body. Various algorithms and/or techniques may be employed to obtain an IEGM signal, a respiration signal, and parameters from either signal.

It also should be appreciated from the above that the various structures and functions described herein may be incorporated into a variety of apparatuses (e.g., a stimulation device, a monitoring device, a lead, etc.) and implemented in a variety of ways. Different embodiments of a device may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described functions or components.

Moreover, some of the operations described herein may be performed by a device that is located externally with respect to the body of the patient. For example, an implanted device may simply send raw sensed data to an external device that then performs appropriate signal processing as taught herein.

The external device may include a communication interface that enables the external device to communicate (e.g., via a telephone line, a data network, a wireless network, etc.) with some other device (e.g., a server). In this way, the external device may send the raw data and/or an indication of pulmonary edema to the patient's physician or some other health provider or service.

In some embodiments the external device may comprise a bed-side monitor or some other device that is adapted to readily receive data from an implanted device. Here, the implanted device may be configured to send raw data (e.g., impedance data or IEGM data) to the external device. Advantageously, this data transfer may occur as the data is being collected when the patient is sleeping. The external device may then be configured to, for example, process the raw data and generate a pulmonary edema indication, as necessary. In response to such an indication the external device may generate a warning signal and/or send the indication and/or raw data to another device (e.g., as discussed above).

The components and functions described herein may be connected and/or coupled in many different ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of detecting pulmonary edema in a patient, comprising:
    determining whether a condition for detecting pulmonary edema is satisfied;
    acquiring an intracardiac electrogram signal when the condition is satisfied;
    detecting QRS complexes in the intracardiac electrogram signal;
    detecting cycle-to-cycle changes in the integral of the QRS complexes;
    deriving a respiration signal from the cycle-to-cycle changes in the integral of the QRS complexes;
    deriving a respiration parameter from the respiration signal, wherein the respiration parameter comprises at least one of the group consisting of: an amplitude of the respiration signal and a pulse width of the respiration signal; and
    comparing the respiration parameter derived from the respiration signal with a baseline parameter to generate an indication of pulmonary edema.

2. The method of claim 1, wherein deriving the respiration signal further comprises detecting changes in interval-based morphological features associated with the intracardiac electrogram signal and/or detecting cycle-to-cycle changes in individual morphological features associated with the intracardiac electrogram signal.

3. The method of claim 2, wherein deriving the respiration signal further comprises tracking changes in at least one of the group consisting of: a maximum amplitude, a peak-to-peak amplitude, an integral, an A-A interval, an R-R interval, and an A-V interval.

4. The method of claim 1, wherein the indication is generated based on a plurality of preliminary indications of pulmonary edema derived from different parameters.

5. The method of claim 1, further comprising acquiring the intracardiac electrogram signal in an implantable cardiac device using at least one implanted cardiac lead.

6. The method of claim 1, wherein generating the indication further comprises at least one of the group consisting of: storing a parameter in a data memory, generating an audible signal, generating a vibratory signal, generating a tissue tickler signal, and generating a radio frequency signal.

7. The method of claim 1, wherein generating the indication further comprises generating a warning signal using a device located within or external to the patient.

8. The method of claim 1, further comprising providing treatment to the patient in accordance with the indication.

9. An implantable cardiac device, comprising:
    a sensor for sensing whether a condition for detecting pulmonary edema is satisfied;
    an electrode adapted to be implanted in a patient;

a sense circuit coupled to the electrode and adapted to provide an intracardiac electrogram signal; and a signal processor adapted to:

detect QRS complexes in the intracardiac electrogram signal when the condition is satisfied;

detect cycle-to-cycle changes in the integral of the QRS complexes;

derive a respiration signal from the cycle-to-cycle changes in the integral of the QRS complexes;

derive a respiration parameter from the respiration signal, wherein the respiration parameter comprises at least one of the group consisting of: an amplitude of the respiration signal and a pulse width of the respiration signal; and compare the respiration parameter derived from the respiration signal with a baseline parameter to generate an indication of pulmonary edema.

10. The device of claim 9, wherein the signal processor is further adapted to detect changes in interval-based morphological features associated with the intracardiac electrogram signal and/or detect cycle-to-cycle changes in individual morphological features associated with the intracardiac electrogram signal.

11. The device of claim 9, further comprising a data memory adapted to store a baseline parameter, and a comparator adapted to compare a parameter derived from the respiration signal with the baseline parameter.

* * * * *